(12) United States Patent
Smith et al.

(10) Patent No.: US 8,092,374 B2
(45) Date of Patent: Jan. 10, 2012

(54) VARIABLY FLEXIBLE INSERTION DEVICE AND METHOD FOR VARIABLY FLEXING AN INSERTION DEVICE

(76) Inventors: Kevin Smith, Coral Gables, FL (US); Derek Deville, Miami, FL (US); Korey Kline, Miami, FL (US); Matthew Palmer, Miami, FL (US)

( * ) Notice: Subject to any disclaimer, the term of this patent is extended or adjusted under 35 U.S.C. 154(b) by 473 days.

(21) Appl. No.: 11/367,607

(22) Filed: Mar. 2, 2006

(65) Prior Publication Data
US 2007/0208364 A1    Sep. 6, 2007

(51) Int. Cl.
*A61B 1/00* (2006.01)
*A61B 1/04* (2006.01)
*A61M 25/00* (2006.01)

(52) U.S. Cl. ......... 600/144; 600/114; 600/184; 604/523

(58) Field of Classification Search .................. 606/108, 606/184; 600/141, 114, 115, 138, 139, 125, 600/140, 187, 121–124, 143, 144–152, 142; 604/95.01, 95.04, 97.01, 98.01, 104, 165.01, 604/171, 173, 176, 118, 523–526, 531, 533, 604/534, 164.13, 165.02, 156, 164.03, 528, 604/236
See application file for complete search history.

(56) References Cited

U.S. PATENT DOCUMENTS

| | | | |
|---|---|---|---|
| 3,557,780 A * | 1/1971 | Sato | .............................. 600/141 |
| 3,998,216 A | 12/1976 | Hosono | |
| 4,176,662 A | 12/1979 | Frazer | |
| 4,575,185 A | 3/1986 | Wentzell et al. | |
| 4,753,223 A | 6/1988 | Bremer | |
| 4,762,118 A * | 8/1988 | Lia et al. | ........................ 600/141 |
| 4,815,450 A | 3/1989 | Patel | |
| 4,817,613 A | 4/1989 | Jaraczewski | |
| 4,838,859 A * | 6/1989 | Strassmann | ................. 604/95.03 |
| 4,890,602 A | 1/1990 | Hake | |
| 4,893,613 A * | 1/1990 | Hake | ............................. 600/152 |

(Continued)

FOREIGN PATENT DOCUMENTS
WO   2005048814 A2   6/2005

OTHER PUBLICATIONS

International Search Report dated Dec. 17, 2007.

(Continued)

*Primary Examiner* — S. Thomas Hughes
*Assistant Examiner* — Jocelin Tanner
(74) *Attorney, Agent, or Firm* — Mayback & Hoffman, P.C.; Gregory L. Mayback; Rebecca A. Tie

(57) ABSTRACT

A variably flexible insertion device includes a hollow body having a proximal end with an entrance for receiving an instrument and a distal end with a tip for protrusion of the instrument. A device transitions the hollow body between a relatively flexible condition and a relatively stiff condition. Tendons within the hollow body maintain the hollow body in the relatively flexible and relatively stiff conditions. A method for variably flexing an insertion device for receiving an instrument, includes providing a hollow body having inner and outer sleeves defining a space therebetween in which tendons are disposed. Suction is applied to create a vacuum in the space for frictionally locking the tendons in place between the sleeves in a relatively stiff condition of the hollow body. The vacuum is relieved to release the tendons in a relatively flexible condition of the hollow body.

47 Claims, 17 Drawing Sheets

U.S. PATENT DOCUMENTS

| | | | |
|---|---|---|---|
| 4,998,282 A | | 3/1991 | Shishido |
| 5,211,633 A | | 5/1993 | Stouder, Jr. |
| D337,733 S | | 7/1993 | Ewing et al. |
| 5,259,366 A | * | 11/1993 | Reydel et al. ............... 600/124 |
| 5,271,382 A | * | 12/1993 | Chikama ..................... 600/142 |
| 5,337,733 A | * | 8/1994 | Bauerfeind et al. .......... 600/139 |
| 5,386,817 A | * | 2/1995 | Jones ........................... 600/104 |
| 5,577,992 A | * | 11/1996 | Chiba et al. .................. 600/152 |
| 5,759,151 A | | 6/1998 | Sturges |
| 5,807,237 A | | 9/1998 | Tindel |
| 5,873,816 A | | 2/1999 | Kagawa et al. |
| 6,117,068 A | | 9/2000 | Gourley |
| 6,196,967 B1 | | 3/2001 | Lim |
| 6,346,077 B1 | * | 2/2002 | Taylor et al. ................. 600/204 |
| 6,375,654 B1 | | 4/2002 | McIntyre |
| 6,387,044 B1 | | 5/2002 | Tachibana |
| 6,468,203 B2 | | 10/2002 | Belson |
| 6,478,731 B2 | | 11/2002 | Speier |
| 6,506,150 B1 | * | 1/2003 | Ouchi ........................... 600/132 |
| 6,517,477 B1 | * | 2/2003 | Wendlandt ................... 600/114 |
| 6,610,007 B2 | | 8/2003 | Belson et al. |
| 6,645,223 B2 | * | 11/2003 | Boyle et al. .................. 606/200 |
| 6,800,056 B2 | | 10/2004 | Tartaglia et al. |
| 6,802,809 B2 | | 10/2004 | Okada |
| 6,858,005 B2 | * | 2/2005 | Ohline et al. ................. 600/141 |
| 6,942,613 B2 | * | 9/2005 | Ewers et al. .................. 600/114 |
| 6,974,411 B2 | | 12/2005 | Belson |
| 6,984,203 B2 | * | 1/2006 | Tartaglia et al. .............. 600/114 |
| 7,066,880 B2 | | 6/2006 | Wendlandt |
| 7,104,951 B2 | | 9/2006 | Hasegawa et al. |
| 7,435,214 B2 | | 10/2008 | Kucklick |
| 7,811,228 B2 | | 10/2010 | Adams |
| 2002/0002323 A1 | | 1/2002 | Moriyama |
| 2002/0177750 A1 | | 11/2002 | Pilvisto |
| 2003/0135198 A1 | | 7/2003 | Berhow et al. |
| 2004/0044350 A1 | | 3/2004 | Martin |
| 2004/0138529 A1 | | 7/2004 | Wiltshire et al. |
| 2004/0182393 A1 | | 9/2004 | MacMillan |
| 2004/0186350 A1 | * | 9/2004 | Brenneman et al. .......... 600/146 |
| 2005/0075538 A1 | | 4/2005 | Banik et al. |
| 2005/0131279 A1 | | 6/2005 | Boulais |
| 2006/0025652 A1 | | 2/2006 | Vargas |
| 2006/0069346 A1 | | 3/2006 | Smith et al. |
| 2007/0088367 A1 | | 4/2007 | Von Weyman-Scharli |
| 2007/0179339 A1 | | 8/2007 | Gorini et al. |
| 2007/0208300 A1 | | 9/2007 | Pravong et al. |
| 2007/0270648 A1 | | 11/2007 | Smith |
| 2008/0091170 A1 | | 4/2008 | Vargas et al. |
| 2009/0149710 A1 | | 6/2009 | Stefanchik et al. |

OTHER PUBLICATIONS

International Search Report for PCT/US07/75701 dated Aug. 29, 2008.

International Search Report for PCT/US07/12179 dated Sep. 12, 2008.

International Search Report for PCT/US08/068348 dated Oct. 30, 2008.

International Search Report for PCT/US08/064084 dated Dec. 9, 2008.

ASGE Abstract 136, "A Split Overture for Easier Colonoscopy", (author not named) (1983).

International Search Report for PCT/US07/012179 dated Sep. 12, 2008.

International Search Report for PCT/US07/05478 dated Dec. 17, 2007.

International Search Report for PCT/US07/075701 dated Aug. 29, 2008.

International Search Report for PCT/US/068348 dated Oct. 30, 2008.

* cited by examiner

VARIABLY FLEXIBLE INSERTION DEVICE AND METHOD FOR VARIABLY FLEXING AN INSERTION DEVICE

BACKGROUND OF THE INVENTION

1. Field of the Invention

The invention relates to a variably flexible insertion device and to a method for variably flexing an insertion device. The insertion device may be used to insert an instrument, in particular a scope, such as an endoscope or a colonoscope, into a patient.

2. Description of the Related Art

Various insertion devices for scopes are known in the art. For example, U.S. Pat. No. 6,942,613 to Ewers et al. discloses a shape lockable apparatus and method, in which nestable elements of an overtube are linked by elastic tension wires connected to an actuator to selectively stiffen the overtube for advancing an instrument. Similarly, U.S. Pat. No. 5,759,151 to Sturges uses a spine having cylindrical segments interconnected by a flexible cable. The cable is secured to a controller for selectively stiffening and relaxing the spine. The Ewers et al. and Sturges devices are complicated and have only elastic tension wires or a flexible cable to maintain stiffness.

U.S. Pat. Nos. 6,984,203 and 6,800,056 to Tartaglia et al. teach a guide which advances in a distal portion of a steerable endoscope having a segmented body. Related U.S. Pat. Nos. 6,468,203 and 6,610,007 to Belson et al. disclose a steerable endoscope with a body, a steering control for a distal portion of the body which selects a path within the patients body and a motion controller for a proximal end of the body which assumes the selected curve. A fiber optic imaging bundle or a video camera are disposed in the body. The Tartaglia et al. and Belson et al. devices provide no mechanism for variably stiffening the guide.

U.S. Pat. No. 5,337,733 to Bauerfeind et al. relates to a tubular inserting device with variable rigidity, in which a flexible insertion part has outer and inner walls defining an intermediate space therebetween. Application of a vacuum to the intermediate space causes the inner wall to lie against the outer wall to render the insertion part rigid. The Bauerfeind et al. device relies merely upon contact between the outer and inner walls for rigidity, with no additional stiffening aid.

ASGE Abstract 136 submitted in 1983 discloses a soft-plastic, split, stiffening overtube to be placed over a colonoscope at any point during the examination.

SUMMARY OF THE INVENTION

It is accordingly an object of the invention to provide a variably flexible insertion device and a method for variably flexing an insertion device, which overcome the hereinafore-mentioned disadvantages of the heretofore-known devices and methods of this general type and in which the device and method are simpler, have more varied uses and are more reliable than the prior art.

With the foregoing and other objects in view there is provided, in accordance with the invention, a variably flexible insertion device. The device comprises a hollow body having a proximal end with an entrance for receiving an instrument, such as a scope, and a distal end with a tip for protrusion of the instrument. A device is provided for transitioning the hollow body between a relatively flexible condition and a relatively stiff condition. Tendons are disposed within the hollow body for maintaining the hollow body in the relatively flexible and relatively stiff conditions.

With the objects of the invention in view, there is also provided a method for variably flexing an insertion device for receiving an instrument. The method comprises providing a hollow body having inner and outer sleeves defining a space therebetween and providing tendons in the space. Suction is applied to create a vacuum in the space for frictionally locking the tendons in place between the inner and outer sleeves in a relatively stiff condition of the hollow body. The vacuum is relieved to release the tendons in a relatively flexible condition of the hollow body.

In accordance with another feature of the invention, the hollow body has an inner sleeve and an outer sleeve defining a space therebetween at least partly surrounding the tendons, and the transitioning device, such as a vacuum port communicating with said space, applies suction to the space for frictionally locking the tendons in place. Vertebrae may be disposed within the hollow body for guiding the tendons.

In accordance with a further feature of the invention, the hollow body has a handle and a flexible section with a given length. The tendons extend substantially entirely over said given length. The tendons float in said handle when said hollow body is in said relatively flexible condition, but are rigidly attached at said distal end. The tendons are not under tension both in said relatively flexible and in the relatively stiff conditions.

In accordance with an added feature of the invention, vertebrae are disposed within said hollow body for guiding said tendons. The vertebrae include a distal-most vertebra at which said tendons are attached.

In accordance with an additional feature of the invention, the hollow body may have a longitudinal slit formed therein for radially loading the hollow body onto the instrument. The slit may be sealed by a closure, such as a slide or press zipper used for plastic storage bags, permitting the device to be resealed after the hollow body has been loaded.

In accordance with yet another feature of the invention, the hollow body has a coil for maintaining a circular cross section. The coil may be a bookbinding-type coil to permit loading of the hollow body on the instrument. Such a bookbinding-type coil is known as a ring wire, double wire, double loop or twin loop binding.

In accordance with yet a further feature of the invention, the hollow body has a handle, a distal end cap to accommodate differently sized instruments, and a flexible portion having a predetermined length in a longitudinal direction between said handle and said distal end cap. The hollow body and said tendons extend entirely along said predetermined length.

In accordance with yet an added feature of the invention, locking pads encircle said tendons in a friction lock area transversely to said longitudinal direction for frictionally locking said tendons in place in addition to said friction locking by said inner and outer sleeves.

In accordance with a concomitant feature of the invention, the handle is an outer handle and the hollow body has an inner handle within said outer handle. The inner handle has channel grooves permitting movement of said tendons. The inner handle has a groove formed therein receiving an O-ring for sealing a space between said outer handle and said inner handle.

Therefore, according to the invention, both a transitioning device using a vacuum to cause contact between the inner and outer sleeves and tendons supporting the stiffening but being free of tension, are combined to enhance the reliability of the device. The capability of loading the hollow body onto the instrument at any time during a procedure also exists by virtue of the slit in the hollow body.

Other features which are considered as characteristic for the invention are set forth in the appended claims.

Although the invention is illustrated and described herein as embodied in a variably flexible insertion device and a method for variably flexing an insertion device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 15 is a cross-sectional view taken along a line XV-XV of

FIG. 10, through the vertebrae with the tendons;

DESCRIPTION OF THE PREFERRED EMBODIMENTS

Figure 1:
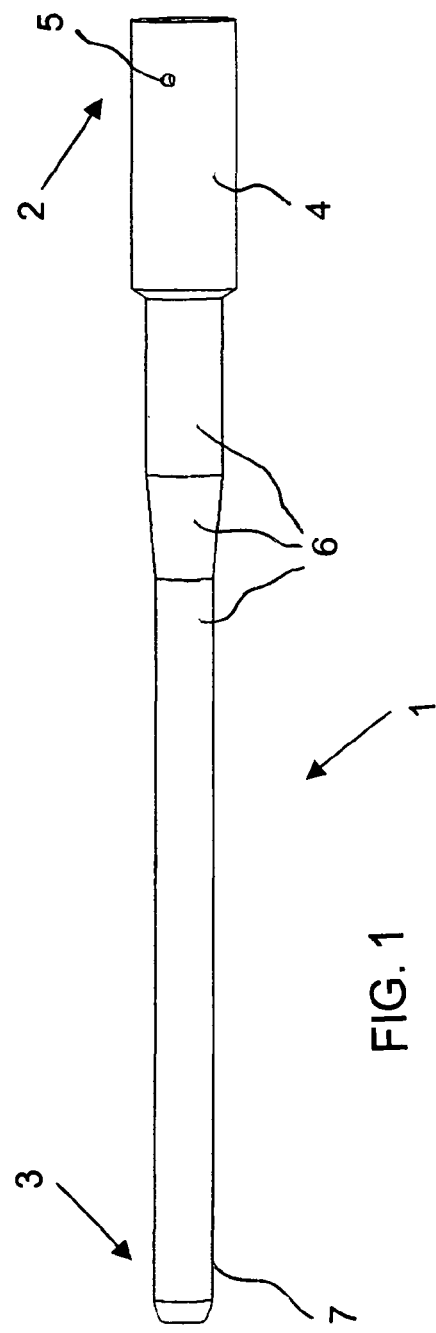
FIG. 1 is a diagrammatic, side-elevational view of a variably flexible insertion device according to the invention.

Referring now to the figures of the drawings in detail and first, particularly, to FIG. 1 thereof, there is seen a variably flexible insertion device 1 according to the invention. The insertion device 1 has a hollow body with a proximal end 2 for manipulation by an operator and for receiving an instrument 32 such as an endoscope or colonoscope seen in FIG. 5. The insertion device 1 also has a distal end 3 for insertion into a patient and for protrusion of the instrument 32. An outer handle 4 of the hollow body for the operator is disposed at the proximal end 2. The handle 4 has a vacuum port 5 formed therein. An outer sleeve 6 of the hollow body is disposed between the outer handle 4 and a nose tip 7 of the hollow body at the distal end 3. The outer sleeve 6 provides a flexible section with a given length extending beyond the handle 4.

Figure 2:
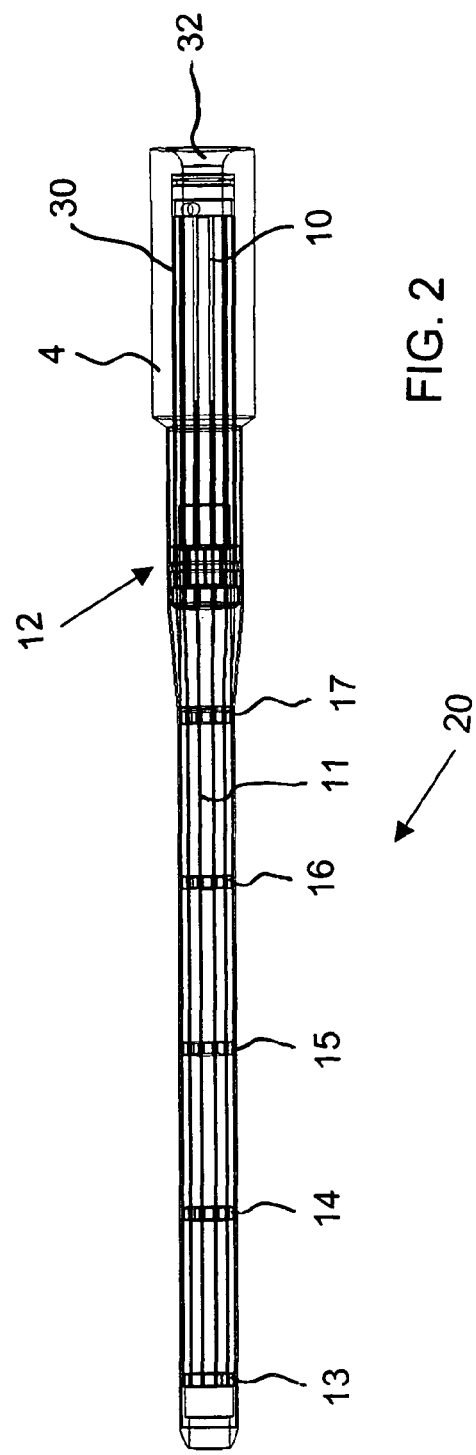
FIG. 2 is a view similar to FIG. 1 showing details of the interior of the insertion device of the invention.

FIG. 2 shows that the outer handle 4 contains an inner handle 30 of the hollow body having channel grooves 10 which permit movement of tendons 11. The tendons 11 extend substantially entirely over the given length of the flexible section provided by the outer sleeve 6. The tendons 11 may have a rounded or flattened cross section or a flattened cross section twisted along its length. A friction lock area 12 is disposed within the outer sleeve 6 for locking the tendons 11 in a manner to be discussed below. Vertebrae 13-17 are distributed along a flexible area 20 which is approximately 30 inches long. Whereas the vertebrae 14-17 allow movement of the tendons 11, the first vertebra 13 closest to the distal end 3 is fixed to the tendons 11. Although six vertebrae are shown, it is understood that more or fewer vertebrae may be provided, for example eight vertebrae, depending on the length of the device 1. The number of tendons 11 is also variable, although twelve is used as an example.

Figure 3:
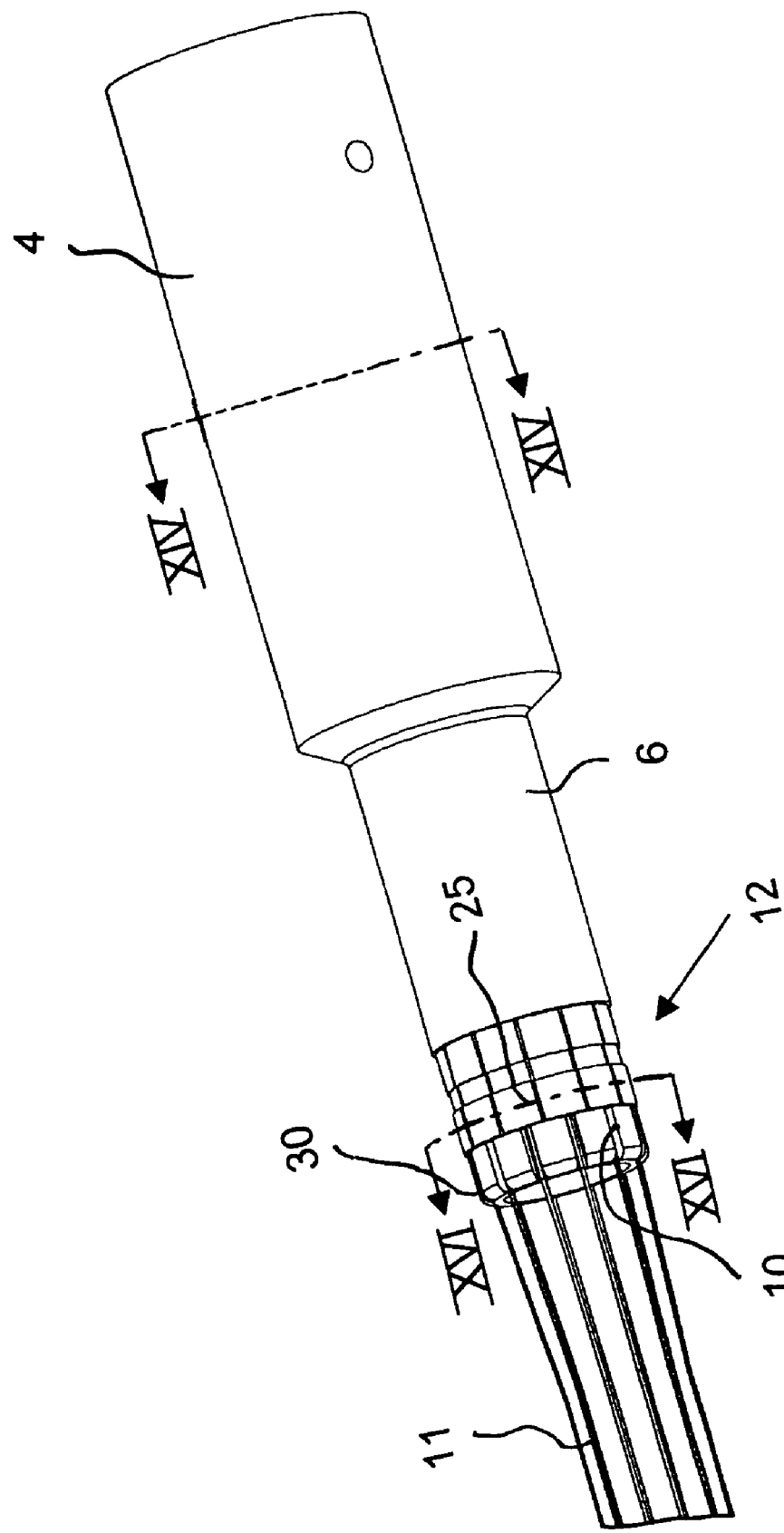
FIG. 3 is an enlarged, fragmentary, perspective view showing inner and outer handles, locking pads and tendons of the insertion device of the invention.
Figure 4:
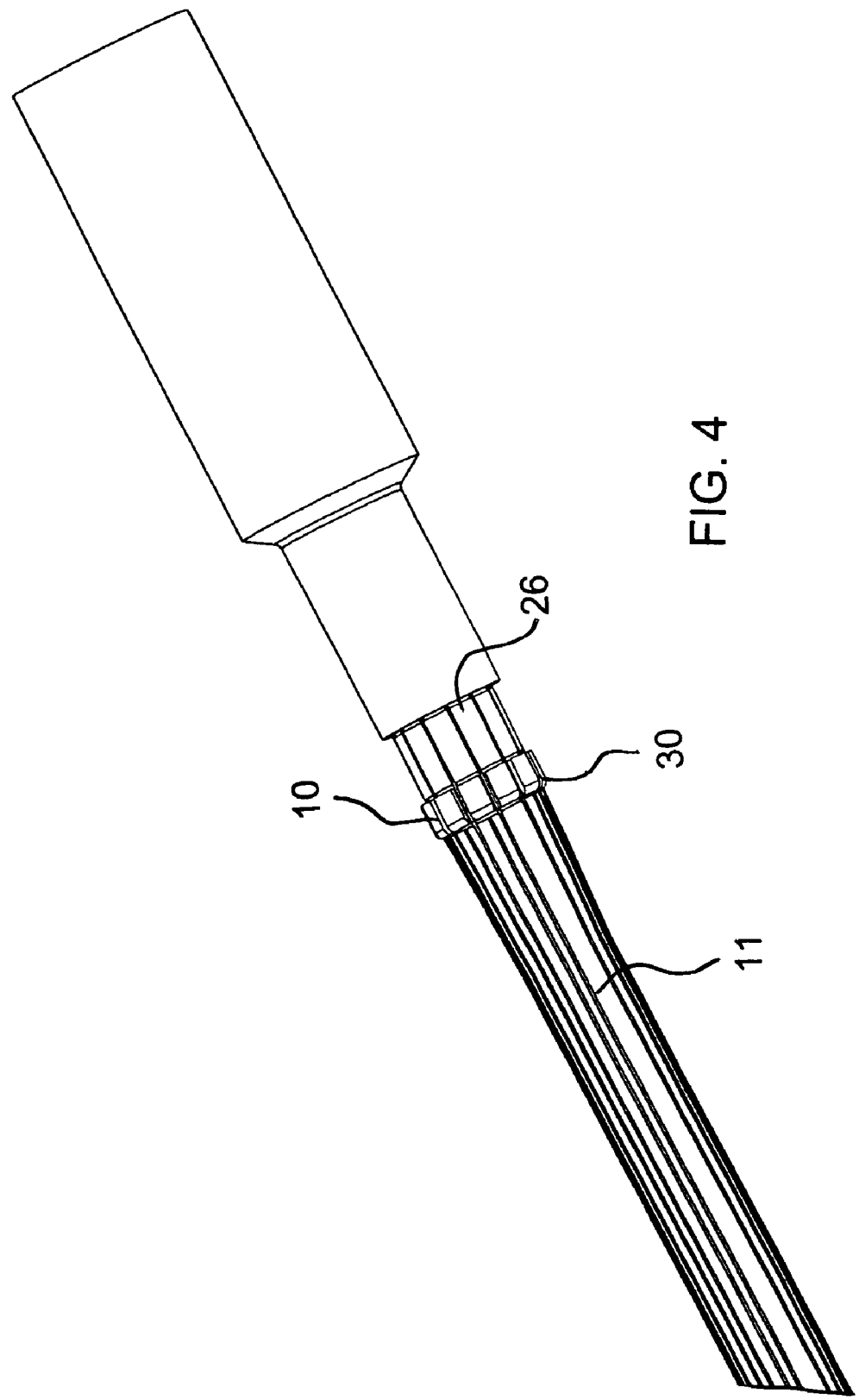
FIG. 4 is a view similar to FIG. 3, showing the inner and outer handles and a friction surface and grooves for the tendons.
Figure 16:
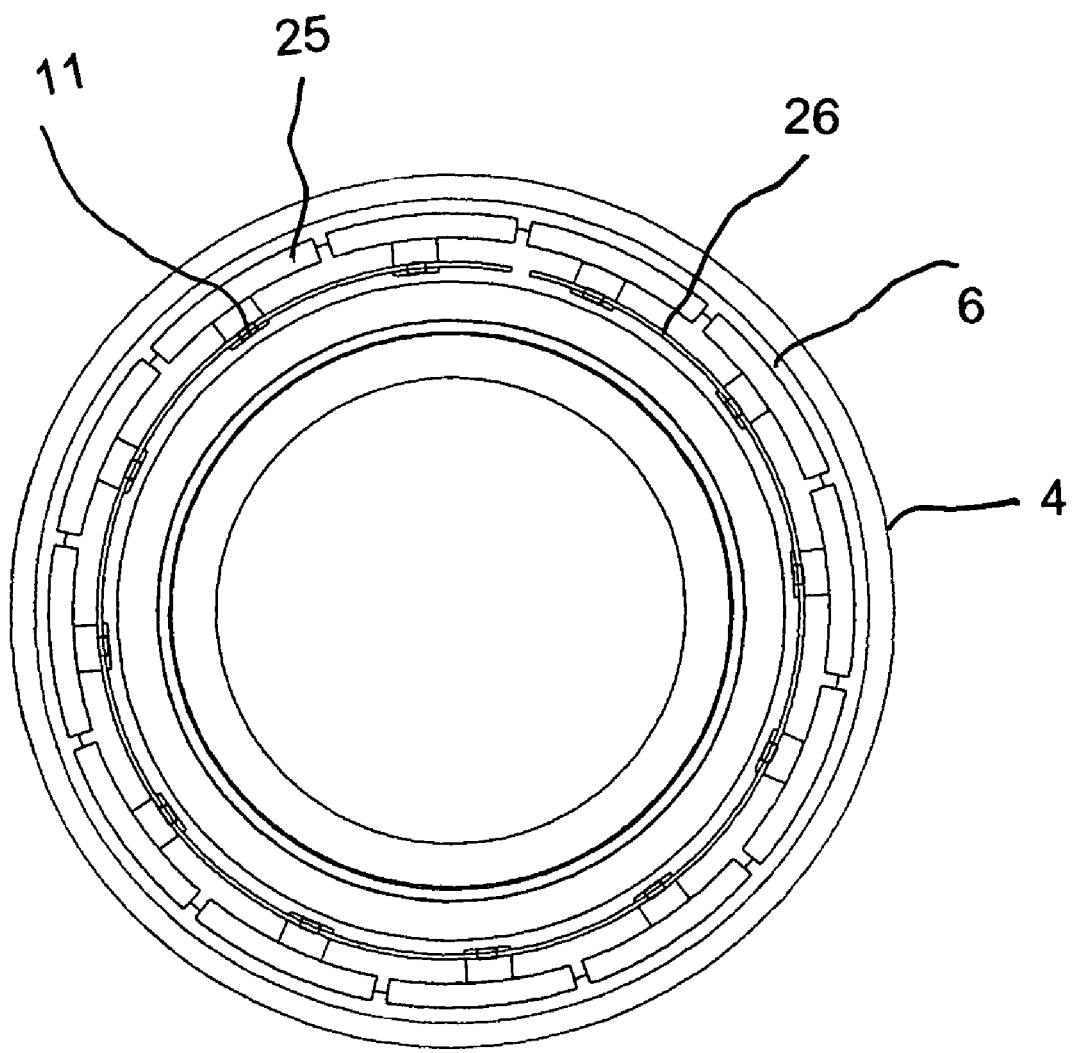
FIG. 16 is a cross-sectional view taken along a line XVI-XVI of FIG. 3, through the vertebrae with the tendons.

As is seen in FIG. 3, a ring of locking pads 25 encircles the friction lock area 12. Each tendon 11 is assigned a respective locking pad 25, which is clearly shown in FIG. 16. The tendons 11 are disposed between the locking pads 25 and a friction surface 26 shown in FIGS. 4 and 16. The friction surface 26 is part of the inner handle 30 having the grooves 10 in which the tendons 11 move.

Figure 5:
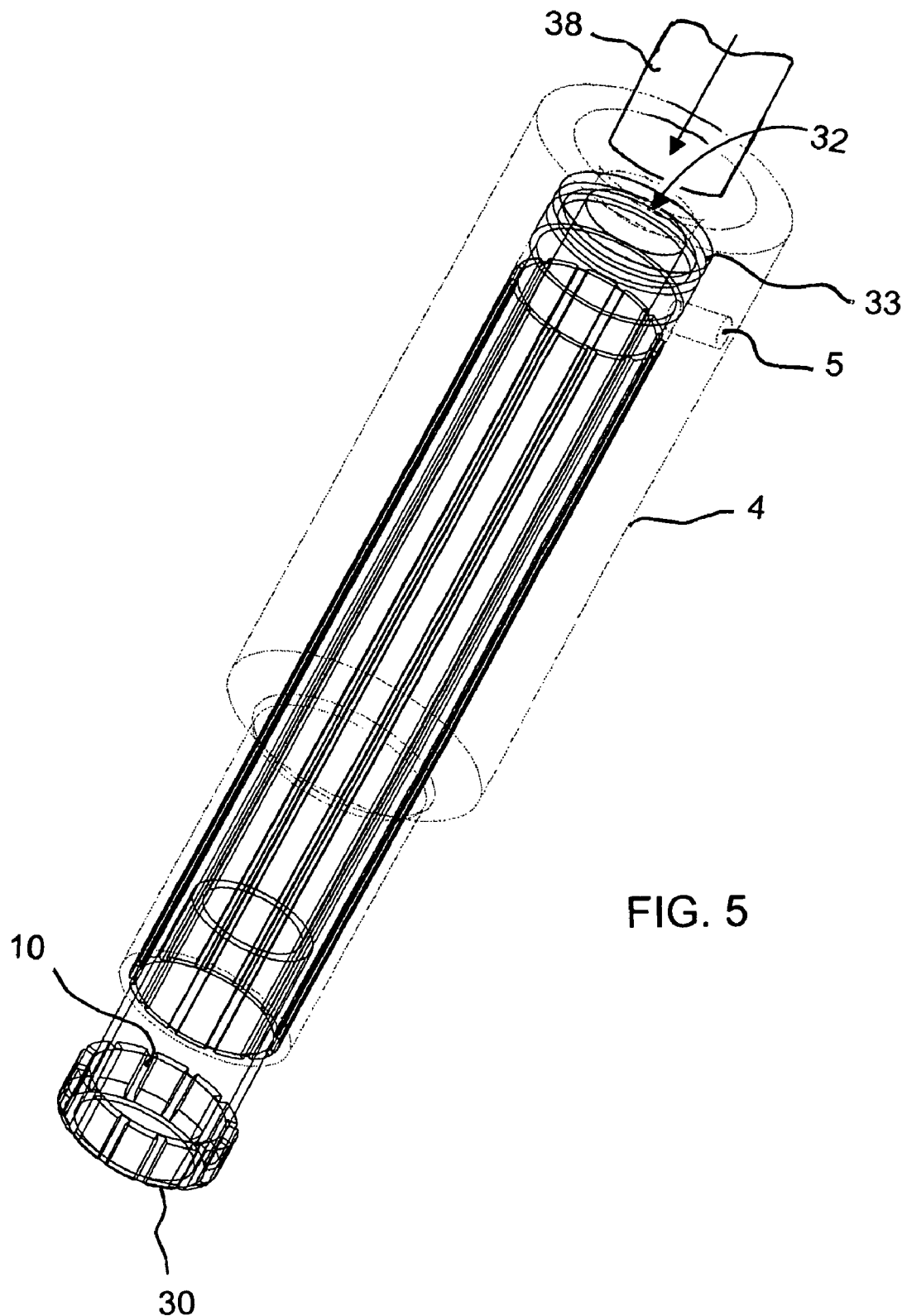
FIG. 5 is a perspective view of a portion of the insertion device of the invention, showing details of the inner and outer handles.

FIG. 5 illustrates the outer handle 4 as well as the inner handle 30 with the channel grooves 10 for the tendons 11. The outer handle 4 is shown as being transparent in FIG. 5, so as to be able to illustrate an entrance 32 for the surgical instrument 38, such as an endoscope or colonoscope, a groove 33 for receiving an O-ring and the vacuum port 5.

Figure 6:
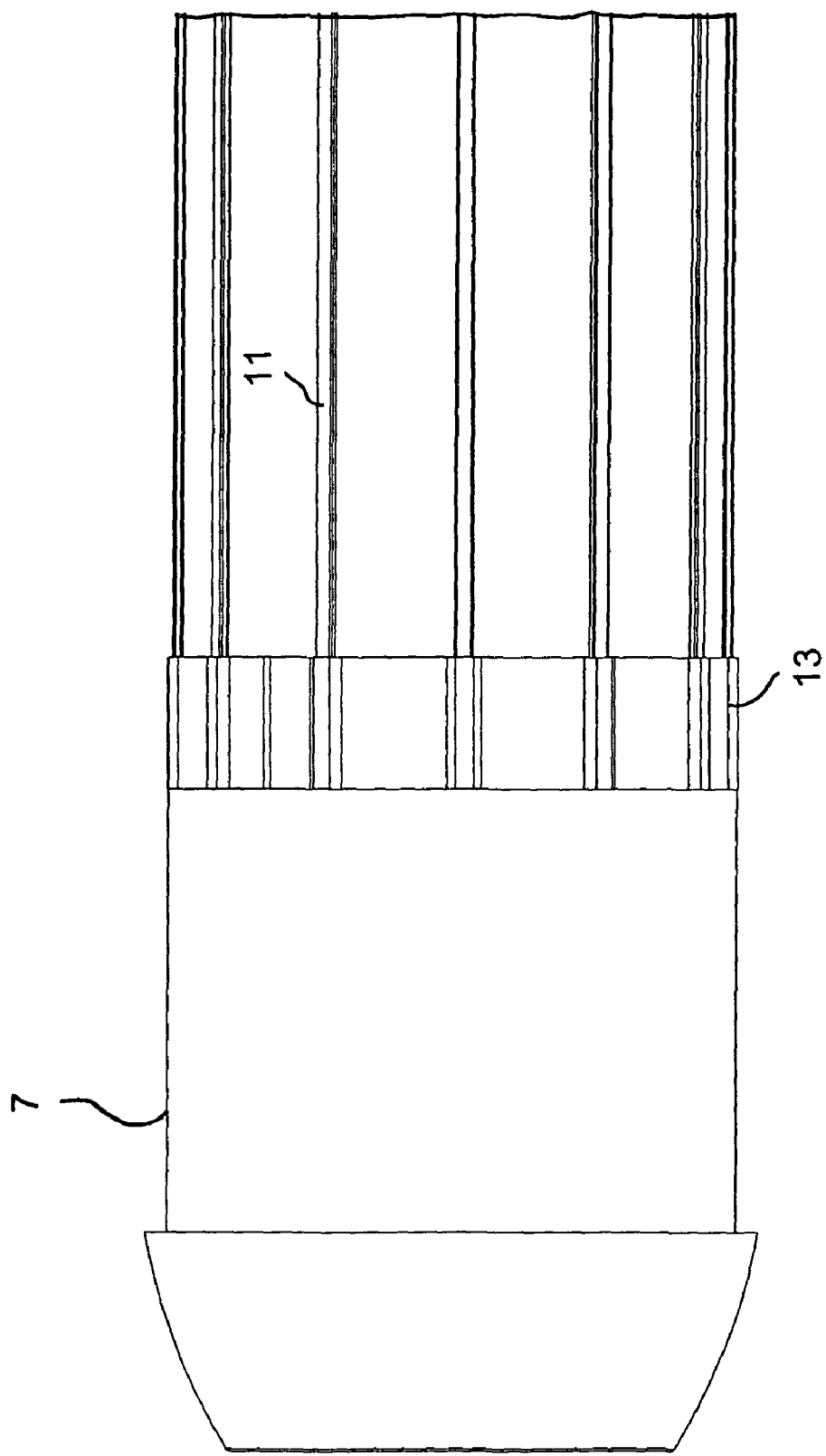
FIG. 6 is an enlarged, fragmentary, side-elevational view of a nose tip and tendons of the insertion device of the invention.
Figure 7:
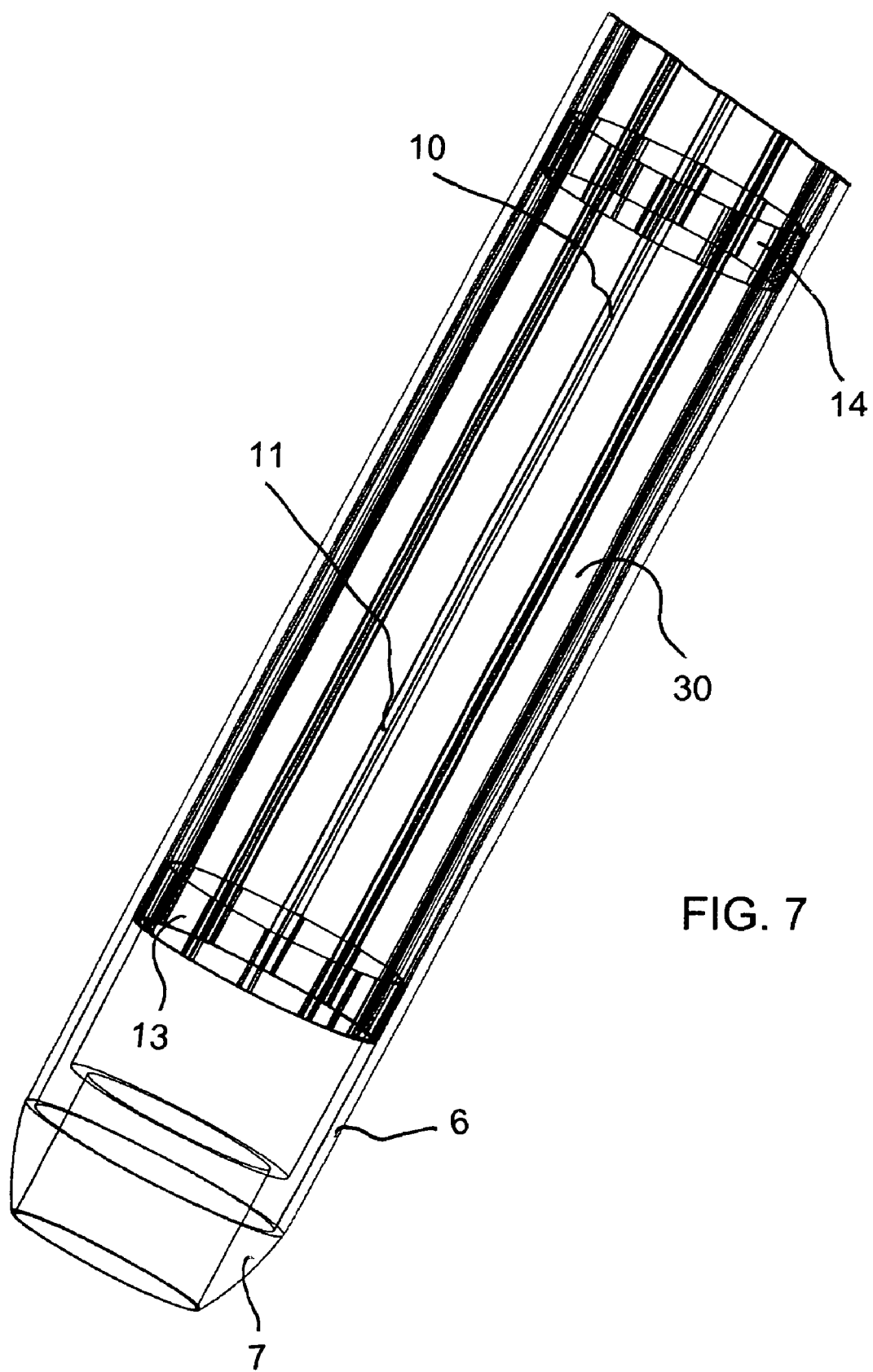
FIG. 7 is a fragmentary, perspective view of the nose tip showing details of the tendons and vertebrae.

FIG. 6 shows the region of the nose tip 7. The tendons 11 are fixed and welded to the first vertebra 13. FIG. 7 also shows the tendons 11 fixed to the first vertebra 13 as well as the second vertebra 14 under which the tendons are free to move in the channel grooves 10 formed in the inner handle 30.

Figure 8:
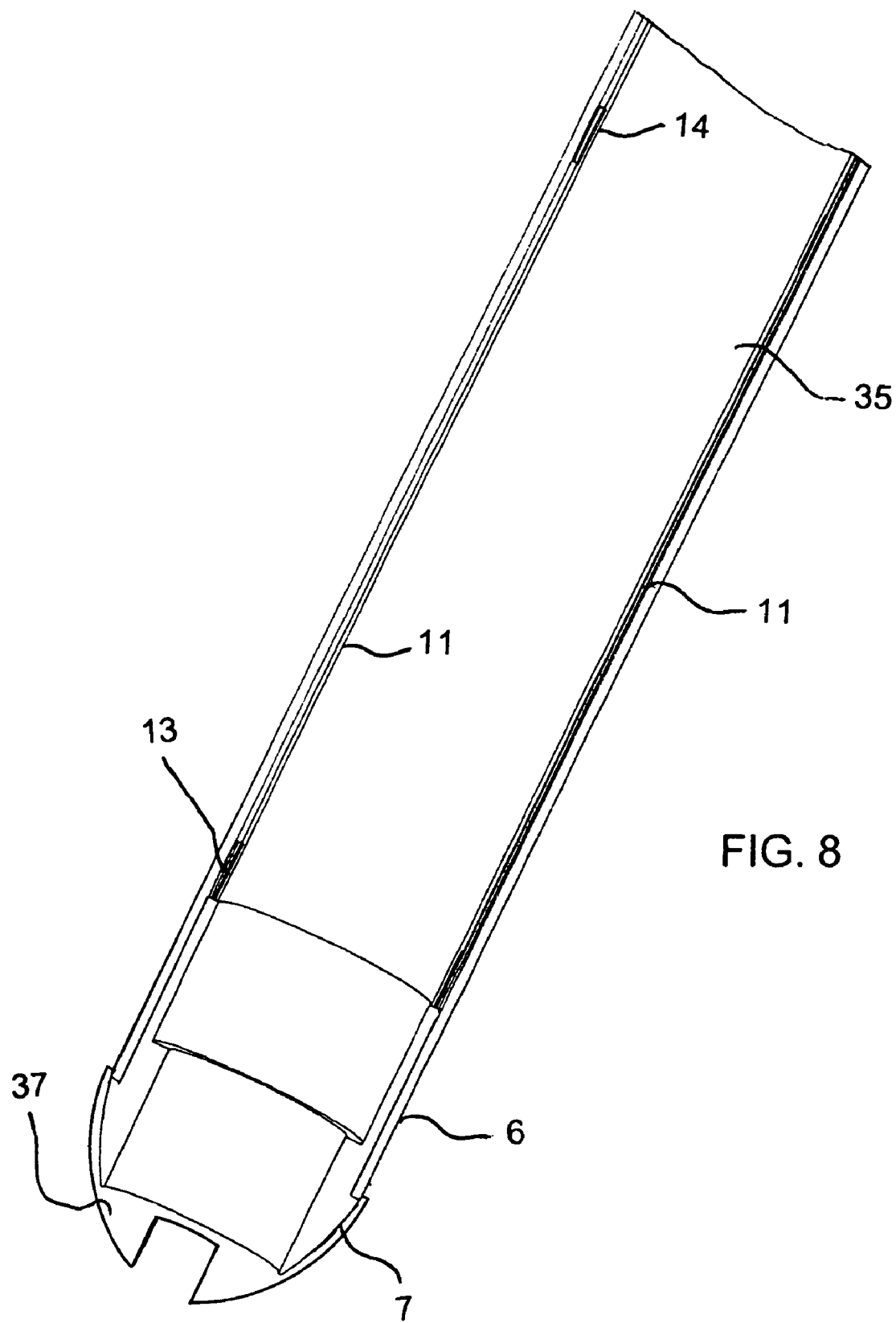
FIG. 8 is a fragmentary, longitudinal-sectional view of the nose tip and vertebrae.

The sectional view of FIG. 8 illustrates the outer sleeve 6, the nose tip 7, two tendons 11, as well as the tendons being welded to the first vertebra 13 and being freely movable in the second vertebra 14. An inner sleeve 35 of the hollow body is also shown in FIG. 8. FIG. 8 additionally shows an end cap 37 to be snapped-on at the distal end to accommodate different sized instruments or scopes 38.

Figure 9:
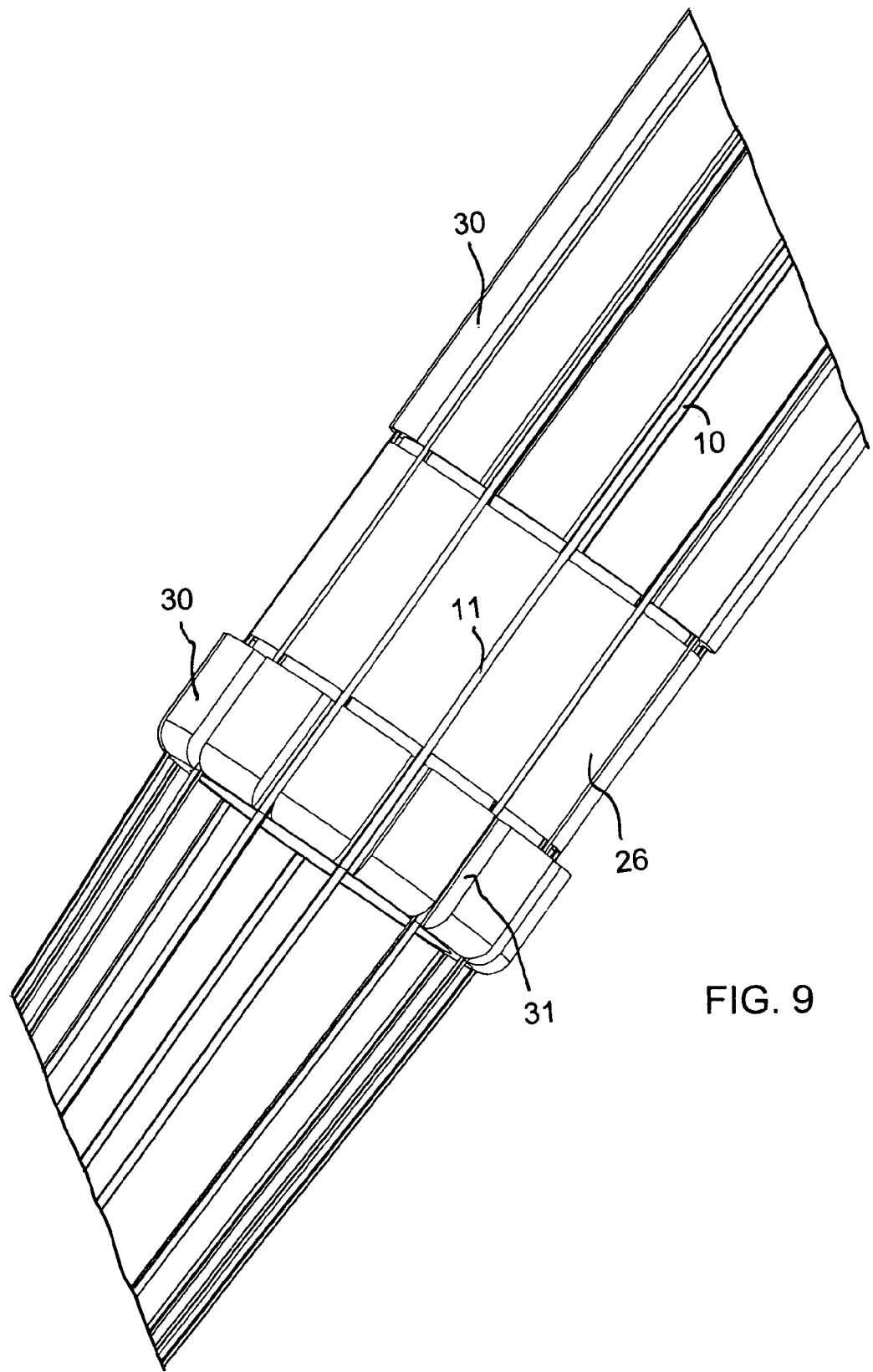
FIG. 9 is an enlarged, fragmentary, perspective view of the tendons over a friction zone.

FIG. 9 shows how the tendons 11 are freely movable in the channel grooves 10 in the inner handle 30 and pass over the friction surface 26.

Figure 10:
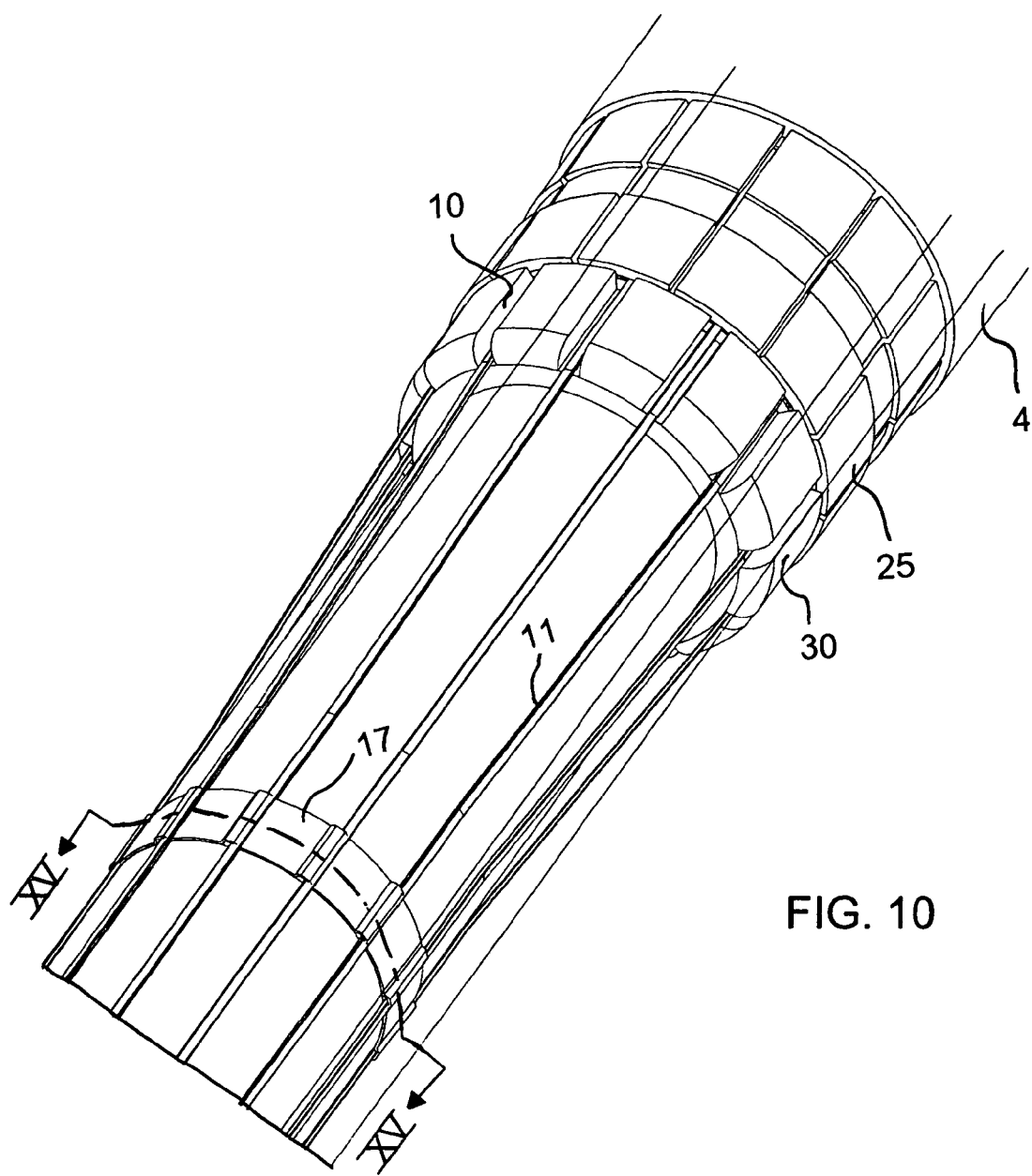
FIG. 10 is a fragmentary, perspective view illustrating the tendons in transition and locking.
Figure 15:
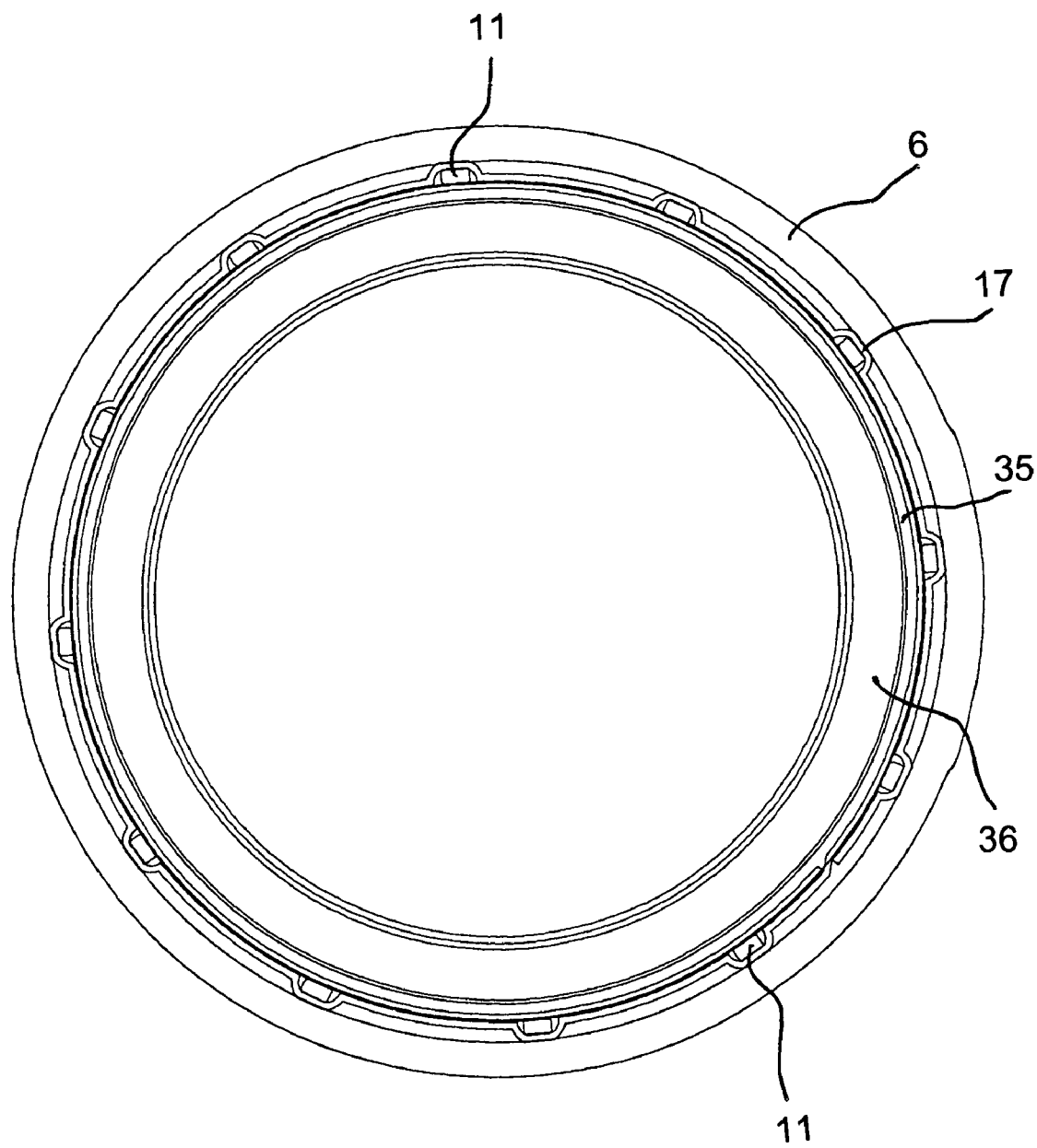

FIG. 10 also shows the friction locking pads 25, the inner handle 30 with the grooves 10 and the tendons 11 passing through the grooves 10 and under the fifth vertebra 17. The cross section of the vertebra 17 illustrated in FIG. 15 additionally shows a coil 36 of the hollow body disposed within and supporting the inner sleeve 35. The coil may be a wire which is TEFLON- or hydrophilic-coated to ease insertion of an endoscope or colonoscope. The stiffness or spring constant k of the coil 36 tends to maintain the device 1 in a straight condition. However, as will be explained in detail below, the device 1 does not remain straight when held horizontal in its flexible state. The coil 36 is used to maintain the round cross section of the device 1 while it is flexed.

Figure 11:
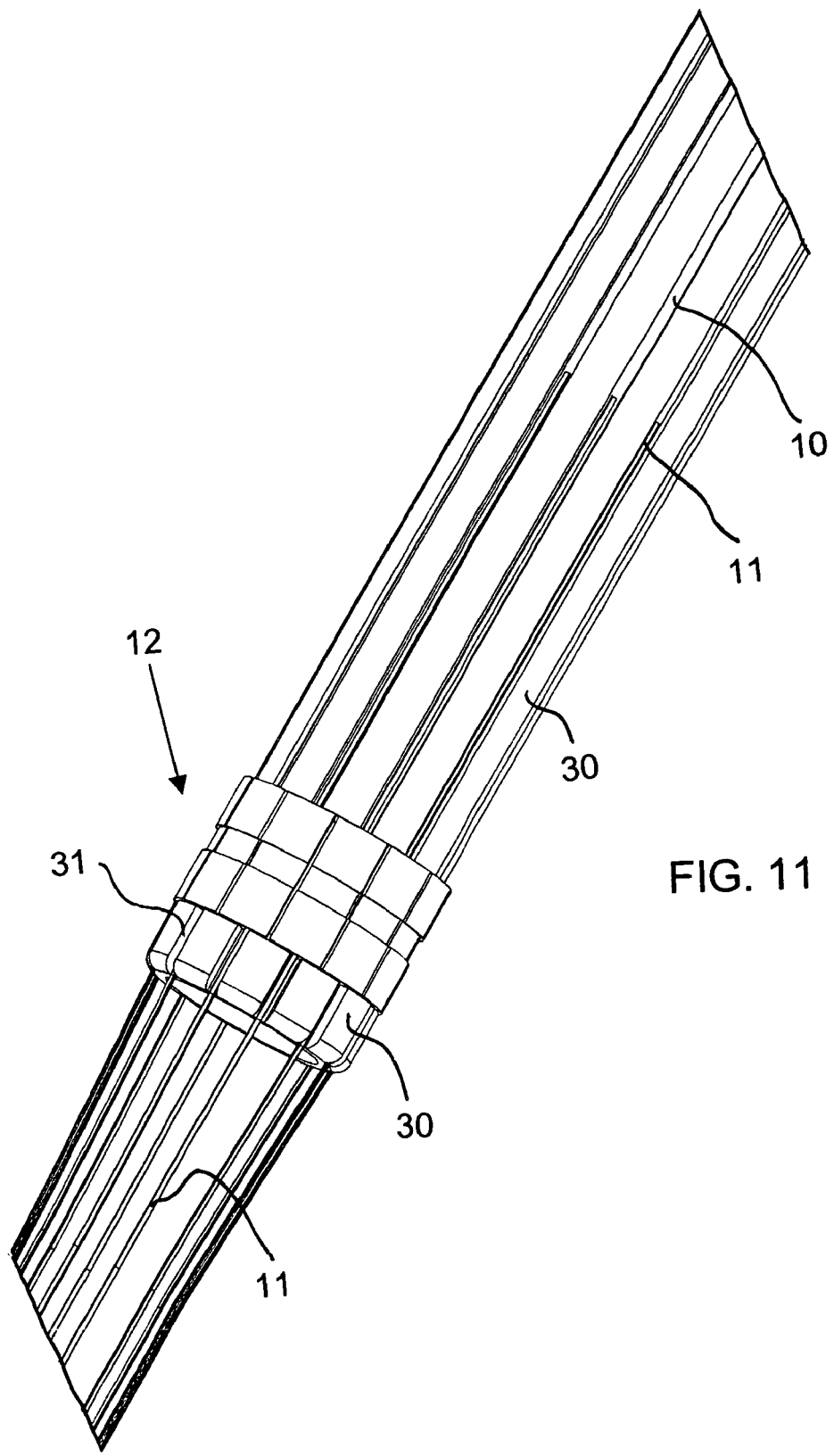
FIG. 11 is a fragmentary, perspective view showing the locking pads for the tendons.

The view of FIG. 11 shows the tendons 11 passing through the channel grooves 10 formed in the inner handle 30 and under the friction locking pads 25. The tendons 11 are freely movable in the channel grooves 10, except when pinched between the friction locking pads 25 and the friction surface 26 in the friction lock area 12.

Figure 12:
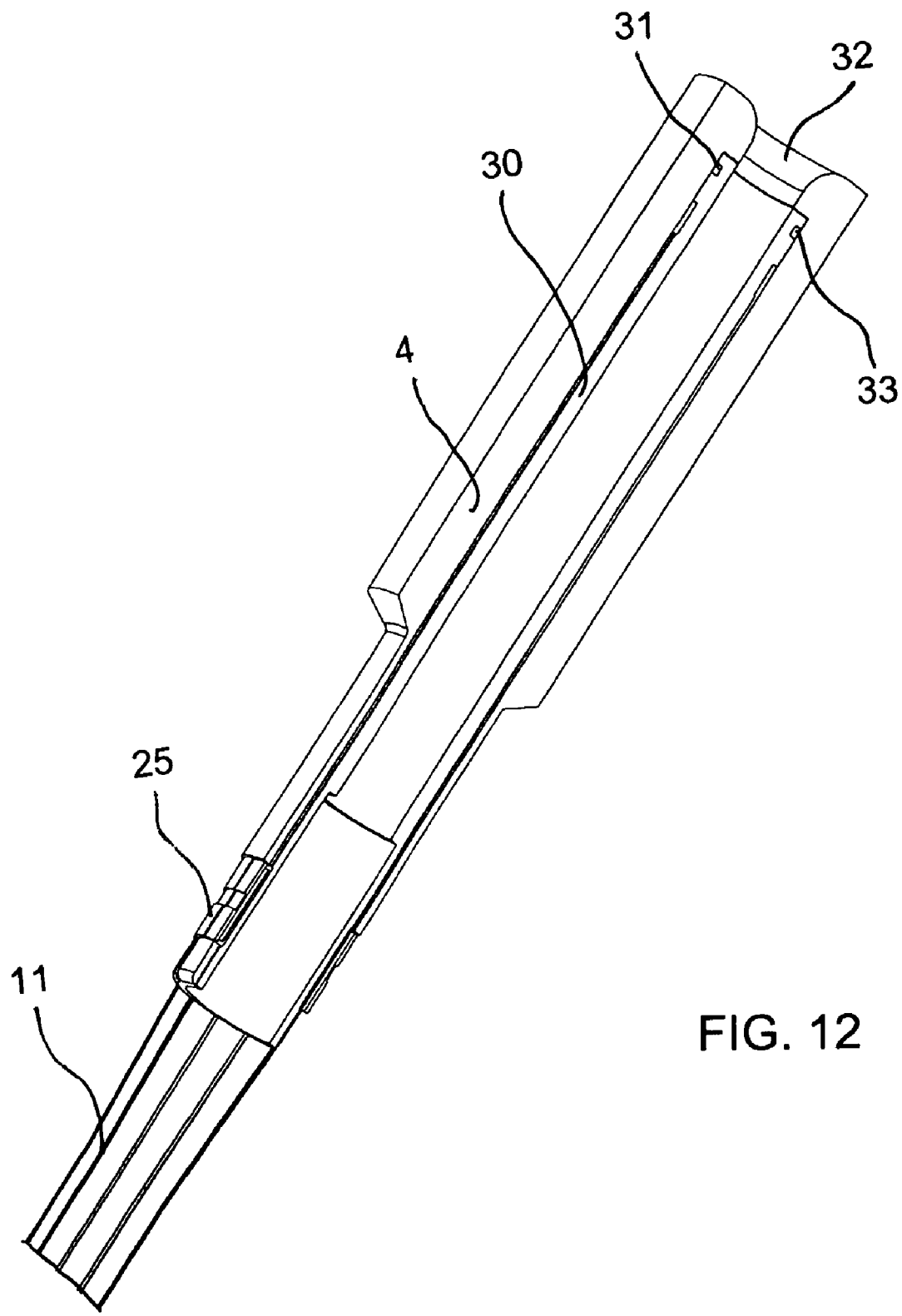
FIG. 12 is a fragmentary, longitudinal-sectional view of the handle.
Figure 14:
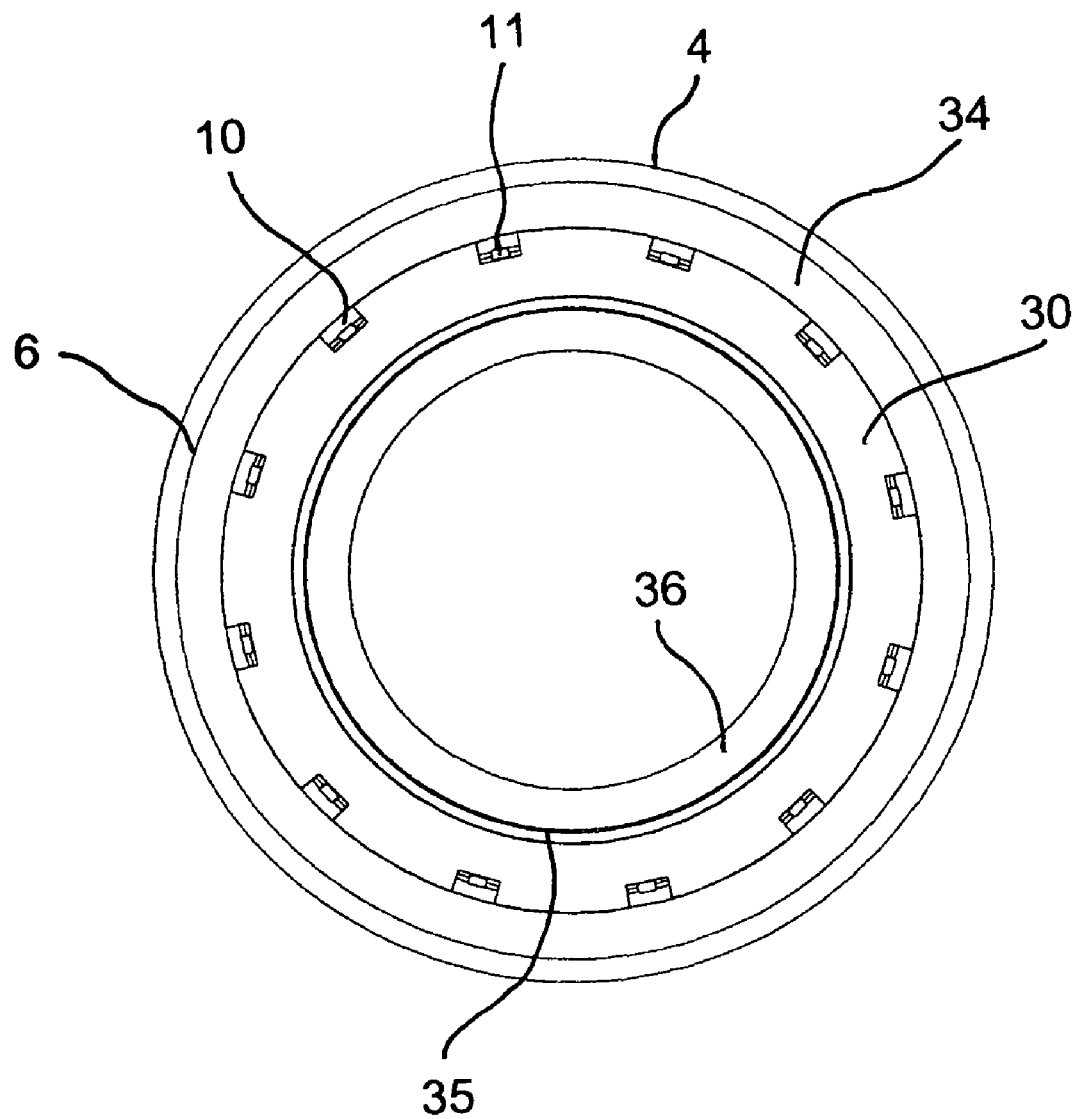
FIG. 14 is a cross-sectional view taken along a line XIV-XIV of FIG. 3, through the handle assembly during transition.

The cross-sectional view of FIG. 12 shows an O-ring 31 disposed in the groove 33. FIG. 14 shows a space 34 between the outer handle 4 and the inner handle 30. The space 34 is sealed by the O-ring 31 and communicates with the vacuum port 5 for applying positive and negative pressure (vacuum) to the space.

Figure 13:
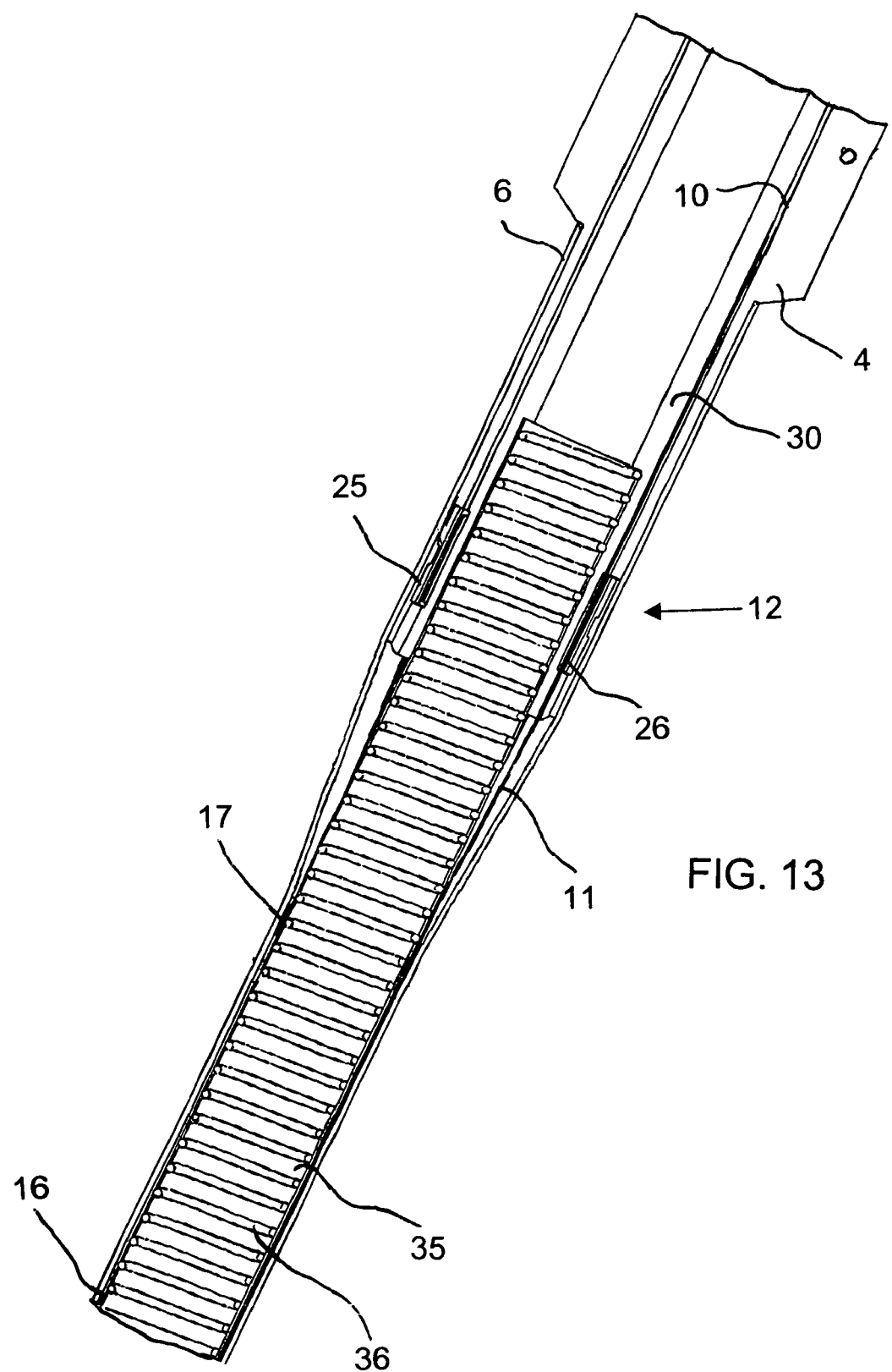
FIG. 13 is a fragmentary, longitudinal-sectional view of a handle locking area.

FIG. 13 is a cross-sectional view illustrating details of the friction lock area 12. It may be seen that the tendons 11 which pass below the vertebrae 16, 17 are pinched between the friction locking pads 25 and the friction surface 26 in the friction area 12.

Figure 18:
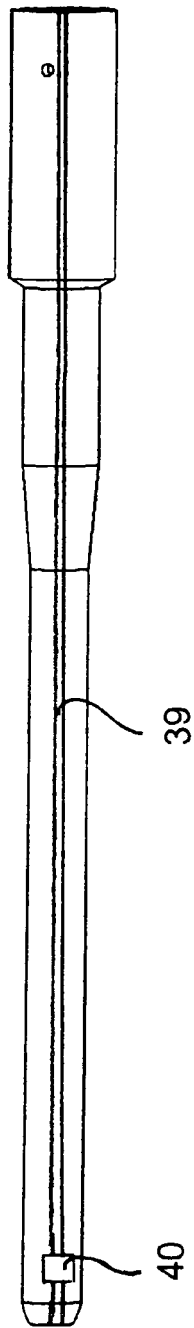
FIG. 18 is a view similar to FIG. 1, showing a slit hollow body with a zipper closure.
Figure 19:
FIG. 19 is a perspective view of a coil used with the embodiment of FIG. 18.

According to another embodiment of the invention which is illustrated in FIG. 18, the hollow body 4, 6, 7, 30, 35, 36 has a longitudinal slit 39 formed therein for radially loading the hollow body onto the instrument 38. The slit has a closure 40, such as a slide or press zipper used for plastic storage bags, permitting the device to be resealed after the hollow body has been loaded. The coil in this case is a ring wire, double wire, double loop or twin loop binding 41 seen in FIG. 19, such as is used for notebooks.

Figure 17:
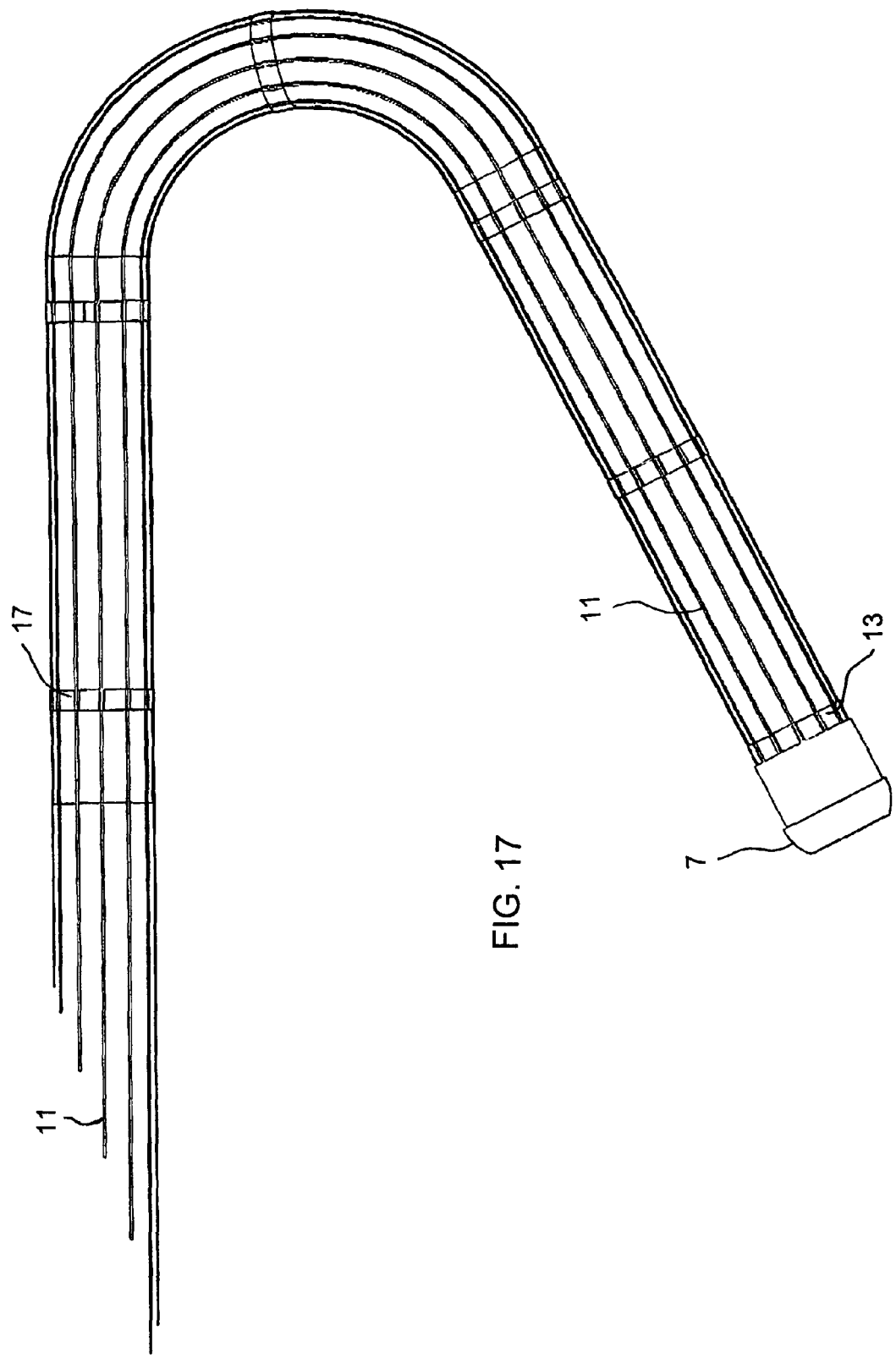
FIG. 17 is a fragmentary, side-elevational view of the device in a flexed condition, showing the nose tip, the vertebrae and the effect of bending on the tendons.

The operation of the variably flexible insertion device 1 is best understood by making reference to FIG. 17 in conjunction with the above-described figures. After the device 1 is forced into a flexed condition against the stiffness or spring constant k of the coil 36 as seen in FIG. 17, for example upon traversing the rectosigmoid junction, and it is desired to maintain that flexed condition for guiding an endoscope, such as a colonoscope, vacuum is applied to the space 34 through the vacuum port 5. When suction is applied to create the vacuum, it causes the inner sleeve 35 and the outer sleeve 6 to firmly contact each other with the tendons 11 sandwiched and frictionally locked therebetween. Therefore, the vacuum port 5 acts as a device for transitioning the hollow body 4, 6, 7, 30, 35, 36 between the relatively flexible condition and the relatively stiff condition through the application of a vacuum. Most of the stiffness causing the device 1 to maintain its flexed condition is accomplished by this interaction of the inner and outer sleeves and the tendons. However, additional stiffness may optionally be accomplished by providing the friction locking pads 25 which contract and hold the tendons 11 against the friction surface 26 in the friction area 12. The device 1 therefore maintains its flexed condition. FIG. 17 shows that in the flexed condition, the tendons 11 at the outer periphery of the bend become shorter and the tendons 11 at the inner periphery of the bend become longer, since they are all fixed in place at the first vertebra 13.

The tendons or wires 11 are passive elements which are not in tension at any time. The tendons float within the hollow body when it is in the flexible condition, except at the distal end. The tendons are frictionally locked by the inner sleeve 35 and the outer sleeve 6 when the hollow body is in the stiff condition. However, in both the relatively flexible condition and the relatively stiff condition, the tendons have no active control imposed on them and are not pulled or constrained.

When it is desired to resume flexibility of the device 1, the vacuum in the space 34 is replaced by air at ambient or positive pressure. This causes the inner sleeve 35 and the outer sleeve 6 to release the tendons 11 and allows the stiffness or spring constant k of the coil 36 to place the device 1 into its normally flexible condition. If friction locking pads 25 are used, they also relax and expand, which in turn releases the tendons 11.

The device is intended to be used in a manner similar to prior art devices. Therefore, the device will be placed over the endoscope. The endoscope will then be inserted into the rectum. The device will then be pushed in its flexible condition, to follow the curvature of the scope. The device will then be stiffened, allowing the scope to be pushed forward with less pressure exerted on the colon of the patient. This procedure can be repeated until the scope reaches the cecum.

An alternative use of the device is to aid in small bowel endoscopy. The device is placed over the endoscope. The endoscope is inserted into the patient transorally, through the stomach and then partially into the small bowel. The device is then pushed in its flexible condition, to follow the curvature of the scope. The device is then stiffened, allowing the scope to be pushed forward without the scope looping in the stomach.

Another use of the device is for aiding in access to internal body parts, such as the gallbladder, through an opening of an internal body cavity, such as the stomach. The device is placed over the endoscope. The endoscope is inserted into the patient transorally, through the stomach and then up against the internal surface of the stomach. The device is then pushed in its flexible condition, to follow the curvature of the scope. The device is then stiffened, allowing the surgeon to create an opening in the stomach wall without the scope looping in the stomach. Once the opening is created, the device and the scope can be advanced outside the stomach. The device can then be stiffened to create a stable platform to perform surgical procedures outside of the stomach. The device could contain one or more features (i.e. balloons) for sealing the outer periphery of the device to the stomach wall to prevent gastric fluids from exiting the stomach.

According to the other embodiment of the invention, the device is capable of being loaded on the instrument or scope after the scope is inserted into the patient. In this embodiment, the slit down the length of the device allows it to be loaded on the scope so that the scope is inserted radially into the hollow body.

We claim:

1. A variably flexible insertion device, comprising:
   a hollow body with a given length having a proximal end with an entrance for receiving an instrument, a distal end with a tip for protrusion of the instrument and inner and outer sleeves defining a space therebetween;
   a device for transitioning said hollow body between a relatively flexible condition and a relatively stiff condition;
   tendons in the form of wires disposed within said hollow body and extending substantially entirely over said given length and being free from at least one of said sleeves and at least partly surrounded by said space, wherein said tendons float in said hollow body when said hollow body is in said relatively flexible condition;
   vertebrae disposed within said hollow body and having one or more channel grooves that guide said tendons; and
   said transitioning device applying suction to said space such that said tendons are frictionally locked in place selectively to maintain said hollow body in said relatively flexible and relatively stiff conditions.

2. The device according to claim 1, wherein said hollow body has a handle and a flexible section with a given length, and said tendons extend substantially entirely over said given length.

3. The device according to claim 2, wherein said handle is an outer handle, said hollow body has an inner handle within said outer handle, and said inner handle has channel grooves permitting movement of said tendons.

4. The device according to claim 3, wherein said inner handle has a groove formed therein receiving an O-ring for sealing a space between said outer handle and said inner handle.

5. The device according to claim 1, wherein said hollow body has a handle, and said tendons are rigidly attached at said distal end and allowed to float at said handle.

6. The device according to claim 5, wherein said tendons are attached to one of said vertebrae.

7. The device according to claim 5, which further comprises locking pads encircling said tendons in a friction lock area transversely to said longitudinal direction for frictionally locking said tendons in place in addition to said friction locking by said inner and outer sleeves.

8. The device according to claim 1, wherein said vertebrae include a distal-most vertebra at which said tendons are attached.

9. The device according to claim 1, wherein said hollow body has a coil for maintaining a circular cross section.

10. The device according to claim 1, wherein said tendons are not in tension or compression when said hollow body is in said relatively stiff condition.

11. The device according to claim 1, wherein said hollow body has a handle, a distal end cap to accommodate differently sized instruments, and a flexible portion having a predetermined length in a longitudinal direction between said handle and said distal end cap, said hollow body and said tendons being extended entirely along said predetermined length.

12. The device according to claim 1, which further comprises locking pads encircling said tendons in a friction lock area for frictionally locking said tendons in place in addition to said friction locking by said inner and outer sleeves.

13. The device according to claim 1, wherein said transitioning device is a vacuum port communicating with said space.

14. The device according to claim 1, wherein the instrument is a scope.

15. The device according to claim 1, wherein said tendons are not under tension in both said relatively flexible and relatively stiff conditions.

16. The device according to claim 1, wherein said tendons are free from both of said sleeves.

17. The device according to claim 1, wherein said tendons are engaged only when suction is applied to said space.

18. The device according to claim 1, wherein said wires move longitudinally.

19. The device according to claim 1, wherein said hollow body has a handle at said proximal end, said wires are free to move longitudinally in said handle, and at least some of said wires are adjusted individually in length for steering said distal end.

20. The device according to claim 1, wherein said wires slide in said relatively flexible and relatively stiff conditions.

21. The device according to claim 1, wherein said wires, said vertebrae and said inner and outer sleeves are all flexible.

22. A method for variably flexing an insertion device for receiving an instrument, the method comprising the following steps:
   providing a hollow body having inner and outer sleeves defining a space therebetween;
   providing tendons in the form of wires in the space being free from at least one of the sleeves and at least partly surrounded by the space;
   applying suction to create a vacuum in the space for frictionally locking the tendons in place between the inner and outer sleeves in a relatively stiff condition of the hollow body; and
   relieving the vacuum to release the tendons in a relatively flexible condition of the hollow body wherein the tendons float in the hollow body when the hollow body is in the relatively flexible condition.

23. The method according to claim 22, which further comprises maintaining a circular cross section of the hollow body with a coil.

24. The method according to claim 22, wherein the tendons are not in tension or compression when the hollow body is in the relatively stiff condition.

25. The method according to claim 22, which further comprises encircling the tendons with locking pads in a friction lock area, and frictionally locking the tendons in place with the locking pads in addition to the friction locking by the inner and outer sleeves.

26. The method according to claim 22, wherein the instrument is a scope.

27. The method according to claim 22, which further comprises maintaining the tendons in a non-tensioned state in both the relatively stiff and the relatively flexible conditions of the hollow body.

28. The method according to claim 22, wherein the tendons are free from both of the sleeves.

29. The method according to claim 22, wherein the tendons are engaged only when suction is applied to the space.

30. The method according to claim 22, which further comprises guiding the wires with vertebrae disposed within the hollow body, and the wires, the vertebrae and the inner and outer sleeves are all flexible.

31. The method according to claim 22, wherein the hollow body has distal and proximal ends and a handle at said proximal end, the wires are free to move longitudinally within the handle, and at least some of the wires are adjusted individually in length for steering the distal end.

32. The method according to claim 22, wherein the wires slide in the relatively flexible and relatively stiff conditions.

33. The method according to claim 22, wherein the wires move longitudinally.

34. A variably flexible insertion device, comprising:
   a hollow body having a proximal end with an entrance for receiving a proximal portion of an instrument, a distal end with a tip for protrusion of a distal portion of the instrument and inner and outer sleeves defining a space therebetween, and said hollow body having a longitudinal slit formed therein for radially loading said hollow body onto the instrument;
   a device for transitioning said hollow body between a relatively flexible condition and a relatively stiff condition;
   tendons in the form of wires disposed within said hollow body and being free from at least one of said sleeves and at least partly surrounded by said space, wherein said tendons float in said hollow body when said hollow body is in said relatively flexible condition; and
   said transitioning device applying suction to said space for frictionally locking said tendons in place selectively to maintain said hollow body in said relatively flexible and relatively stiff conditions.

35. The device according to claim 34, wherein said tendons are not under tension in both said relatively flexible and relatively stiff conditions.

36. The device according to claim 34, wherein said slit has a closure permitting said slit to be resealed after said hollow body has been loaded.

37. The device according to claim 36, wherein said closure is a slide or press zipper.

38. The device according to claim 34, wherein said hollow body has a ring wire coil for maintaining a circular cross section and permitting said hollow body to be loaded.

39. The device according to claim 34, wherein said tendons are free from both of said sleeves.

40. A method for variably flexing an insertion device for receiving an instrument, the method comprising the following steps:
   providing a hollow body having inner and outer sleeves defining a space therebetween, the hollow body having a longitudinal slit formed therein;
   providing tendons in the form of wires in the space being free from at least one of the sleeves and at least partly surrounded by the space;
   loading the hollow body radially onto the instrument through the slit;
   applying suction to create a vacuum in the space for frictionally locking the tendons in place between the inner and outer sleeves in a relatively stiff condition of the hollow body; and
   relieving the vacuum to release the tendons in a relatively flexible condition of the hollow body wherein the tendons float in the hollow body when the hollow body is in the relatively flexible condition.

41. The device according to claim 34, wherein said tendons are engaged only when suction is applied to said space.

42. The method according to claim 41, which further comprises maintaining the tendons in a non-tensioned state in both the relatively stiff and the relatively flexible conditions of the hollow body.

43. The method according to claim 41, which further comprises resealing the slit with a closure after the hollow body has been loaded.

44. The method according to claim 43, wherein the closure is a slide or press zipper.

45. The method according to claim 41, which further comprises placing a ring wire coil in the hollow body for maintaining a circular cross section of the hollow body and permitting the hollow body to be loaded.

46. The method according to claim 41, wherein the tendons are free from both of the sleeves.

47. The method according to claim 41, wherein the tendons are engaged only when suction is applied to the space.

\* \* \* \* \*